US012324631B2

(12) United States Patent
Auvray et al.

(10) Patent No.: US 12,324,631 B2
(45) Date of Patent: Jun. 10, 2025

(54) GUIDANCE FOR TREATMENT OF A CHRONIC TOTAL OCCLUSION

(71) Applicant: KONINKLIJKE PHILIPS N.V., Eindhoven (NL)

(72) Inventors: Vincent Maurice André Auvray, Meudon (FR); Raoul Florent, Ville D'Avray (FR); Caroline Denise Francoise Raynaud, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 437 days.

(21) Appl. No.: 17/487,133

(22) Filed: Sep. 28, 2021

(65) Prior Publication Data

US 2022/0096170 A1    Mar. 31, 2022

(30) Foreign Application Priority Data

Sep. 28, 2020 (EP) .................................... 20290067

(51) Int. Cl.
*A61B 34/20* (2016.01)
*A61B 6/00* (2006.01)
(Continued)

(52) U.S. Cl.
CPC .............. *A61B 34/20* (2016.02); *A61B 6/486* (2013.01); *A61B 6/504* (2013.01); *G06T 7/0014* (2013.01);
(Continued)

(58) Field of Classification Search
CPC ......... A61B 34/20; A61B 6/486; A61B 6/504; A61B 2034/2065; A61B 6/481;
(Continued)

(56) References Cited

U.S. PATENT DOCUMENTS 8,290,228 B2 * 10/2012 Cohen .................. A61B 5/0044
382/199
8,463,007 B2 *  6/2013 Steinberg ................ G06T 7/246
382/128
(Continued)

FOREIGN PATENT DOCUMENTS

DE         102007046454 A1   12/2008
EP             3973877 A1 *   3/2022    ............. A61B 34/20
(Continued)

OTHER PUBLICATIONS

Liu, Xuqing et al "Detection and Classification of Chronic Total Occlusion Lesions using Deep Learning", 41st Annual Internation AI Conference of the IEEE Engineering in Medicine and Biology Society, Jul. 2019.
(Continued)

*Primary Examiner* — Manav Seth

(57) ABSTRACT

The present invention relates to a guidance for treatment of a chronic total occlusion. In order to provide improved guidance information for chronic total occlusion treatment, a device (10) for guidance for treatment of a chronic total occlusion is provided that comprises an image supply (12), a data processor (14) and an output (16). The image supply provides a sequence of angiographic images comprising a vascular structure. The data processor detects at least one portion of the vascular structure indicating a total occlusion of a vessel based on the sequence of angiographic images; and determines an image of the sequence of images that shows at least one segment of the vessel next to the total occlusion; and generates guidance image data based on the determined image. The output provides the generated guidance image data. Thus, additional information relating to spatial aspects is provided to the user based on 2D image data.

20 Claims, 3 Drawing Sheets

(51) Int. Cl.
*A61B 6/50* (2024.01)
*G06T 7/00* (2017.01)

(52) U.S. Cl.
CPC ............ *A61B 2034/2065* (2016.02); *G06T 2207/10016* (2013.01); *G06T 2207/10116* (2013.01); *G06T 2207/30101* (2013.01)

(58) Field of Classification Search
CPC ..... A61B 6/487; A61B 6/5235; A61B 6/5247; G06T 7/0014; G06T 2207/30101; G06T 2207/10116; G06T 2207/10016; G06T 7/0016
See application file for complete search history.

(56) References Cited

U.S. PATENT DOCUMENTS

| | | | | |
|---|---|---|---|---|
| 8,542,900 | B2* | 9/2013 | Tolkowsky | A61B 6/504 |
| | | | | 600/513 |
| 8,670,603 | B2* | 3/2014 | Tolkowsky | A61B 34/10 |
| | | | | 600/513 |
| 8,712,505 | B2* | 4/2014 | Ishikawa | A61B 3/102 |
| | | | | 600/452 |
| 8,849,005 | B2* | 9/2014 | Sundar | G06V 40/10 |
| | | | | 382/132 |
| 9,144,394 | B2* | 9/2015 | Cohen | G06T 7/33 |
| 9,700,209 | B2* | 7/2017 | Florent | A61B 90/37 |
| 10,307,061 | B2* | 6/2019 | Cohen | A61B 17/12036 |
| 11,207,042 | B2* | 12/2021 | Auvray | G06T 11/60 |
| 2006/0058643 | A1 | 3/2006 | Florent | |
| 2007/0201609 | A1* | 8/2007 | Ohishi | A61B 6/4441 |
| | | | | 378/4 |
| 2010/0063389 | A1 | 3/2010 | Florent | |
| 2010/0111385 | A1* | 5/2010 | Hummel | G06T 19/20 |
| | | | | 382/128 |
| 2010/0209012 | A1 | 8/2010 | Florent | |
| 2011/0216092 | A1 | 9/2011 | Florent | |
| 2011/0319752 | A1 | 12/2011 | Steinberg | |
| 2014/0114333 | A1* | 4/2014 | Tolkowsky | A61B 5/4836 |
| | | | | 606/159 |
| 2014/0294149 | A1* | 10/2014 | Rieber | G06T 7/0012 |
| | | | | 378/62 |
| 2015/0282890 | A1* | 10/2015 | Cohen | A61B 5/1128 |
| | | | | 600/424 |
| 2019/0159842 | A1* | 5/2019 | Razeto | G06T 7/33 |
| 2019/0343474 | A1* | 11/2019 | Auvray | G06T 7/0012 |
| 2022/0392065 | A1* | 12/2022 | Min | A61B 6/032 |
| 2024/0299155 | A1* | 9/2024 | El-Kurdi | A61F 2/06 |

FOREIGN PATENT DOCUMENTS

| | | | |
|---|---|---|---|
| JP | 2011104056 A | 6/2011 | |
| WO | WO-2008107905 A2 * | 9/2008 | ....... A61B 17/12036 |
| WO | 2015044433 A1 | 4/2015 | |
| WO | WO-2017042068 A1 * | 3/2017 | ............ A61B 34/20 |
| WO | WO-2018127520 A1 * | 7/2018 | ............ A61B 6/463 |

OTHER PUBLICATIONS

Aziz, S. et al Chronic Total Occlusions—a Stiff Challenge Requiring a Major Breakthrough: is there light at the end of the tunnel? Heart, 2005.

* cited by examiner

GUIDANCE FOR TREATMENT OF A CHRONIC TOTAL OCCLUSION

FIELD OF THE INVENTION

The present invention relates to treating chronic total occlusions, and relates in particular to a device for guidance for treatment of a chronic total occlusion, to a system for guidance for treatment of a chronic total occlusion and to a method for guidance for treatment of a chronic total occlusion.

BACKGROUND OF THE INVENTION

An example of a vascular related disease is chronic total occlusion. An example of treatment includes a percutaneously performed intervention. When treating chronic total occlusions percutaneously, the clinician has to steer the guide wire through the occluded region, inside a lumen that is not directly visible. It is necessary for the clinician to pierce the occlusion, while not deriving subintimal, or even rupture the vessel. In this condition, having a good idea of the course of the occluded section is crucial. An example for providing information about the vascular situation is the use of X-ray radiation together with contrast injection. Visualizing vascular structures with contrast agent in the context of treating stenosis are provided in, for example, WO 2008/104909 A1, WO 2009/037638 A2 and WO 2010/044001 A2. However, in total occlusions, contrast agent may not be provided to these portions. In some cases though, the vessel part downstream, i.e. distal to the occlusion, can be made partially visible. This part of the vasculature is sometimes indirectly fed by collaterals originating from the original (occluded) branch or other (non-occluded) branches. In these cases, the branch distal to the occlusion appears faintly at the end of the angiographic sequence. However, the process of carefully examining the angiograms to identify a faint segment distal to the occlusion is tedious.

SUMMARY OF THE INVENTION

There may thus be a need to provide improved guidance information for chronic total occlusion treatment.

The object of the present invention is solved by the subject-matter of the independent claims; further embodiments are incorporated in the dependent claims. It should be noted that the following described aspects of the invention apply also for the device for guidance for treatment of a chronic total occlusion, for the system for guidance for treatment of a chronic total occlusion and for the method for guidance for treatment of a chronic total occlusion.

According to the present invention, a device for guidance for treatment of a chronic total occlusion is provided. The device comprises an image supply, a data processor and an output. The image supply is configured to provide a sequence of angiographic images comprising a vascular structure. The data processor is configured to detect at least one portion of the vascular structure indicating a total occlusion of a vessel based on the sequence of angiographic images. The data processor is also configured to determine an image of the sequence of images that shows at least one segment of the vessel next to the total occlusion. The data processor is further configured to generate guidance image data based on the determined image. Further, the output is configured to provide the generated guidance image data.

As an advantage, the user is provided with additional information about the chronic total occlusion, which information provides guidance to the user in an improved manner.

According to an example, the data processor is configured to determine a first image of the sequence of images that shows a segment of the vessel downstream to the total occlusion. The data processor is also configured to generate guidance image data based on the determined first image.

As an effect, the clinician sees the exit of the occlusion he/she needs to bridge, which makes the likely course of the occluded region easier to infer. The clinician will then direct the guide wire along the vessel course he/she has imagined, to try to reach the non-occluded part while not exiting the occlusion.

According to an example, for the detection of the at least one portion of the vascular structure indicating the total occlusion of a vessel, the data processor is configured to at least one of the group of: comparison of the imaged vasculature with a projected model; or identification of determined vessel parts, measurement of a physical value and comparison of the measured value with a reference value; or extrapolation of branches and detection if extrapolated part matches contrast later in sequence; or to be trained with collection of chronic total occlusion angiograms and manually determined locations thereof and to apply this to new angiograms.

According to an example, the data processor is further configured to determine a region of the image to be displayed based on the at least one portion of the vascular structure indicating the total occlusion. As an option, in addition or alternatively, the generating comprises a zooming-in of the determined first image.

According to an example, the data processor is further configured to determine a second image of the sequence of images that shows a segment of the vessel upstream to the total occlusion. As an option, in addition or alternatively, the data processor is further configured to use the first image and the second image for the generation of the guidance image data. As another option, also in addition or alternatively, the generating comprises showing the first image and the second image.

According to an example, the data processor is configured to determine an image of the sequence of images that shows both a segment of the vessel downstream to the total occlusion and a segment of the vessel upstream to the total occlusion. The data processor is further configured to generate guidance image data based on the determined image.

According to an example, the data processor is further configured to spatially filter the selected images, and use the spatially filtered images for the generation of the guidance image data. Alternatively or in addition, the data processor is further configured to temporally align the images, and combine the temporally aligned images and use them for the generation of the guidance image data.

According to an example, a display is provided configured to display the guidance image data as guidance information.

According to the present invention, also a system for guidance for treatment of a chronic total occlusion is provided. The system comprises a device for guidance for treatment of a chronic total occlusion according to one of the preceding examples. The system also comprises an X-ray imaging arrangement. The X-ray imaging arrangement is configured to provide the sequence of angiographic images.

According to the present invention, also a method for guidance for treatment of a chronic total occlusion is provided. The method comprises the following steps:

providing a sequence of angiographic images comprising a vascular structure;

detecting at least one portion of the vascular structure indicating a total occlusion of a vessel based on the sequence of angiographic images;

determining an image of the sequence of images that shows at least one segment of the vessel next to the total occlusion;

generating guidance image data based on the determined image; and providing the guidance image data to a clinician.

According to an aspect, an angiographic sequence is provided and the plurality of images is checked for an indication of a possible total occlusion, in particular for chronic total occlusions. Such indications may be abnormal short branches or vessels with an interrupted presence of contrast agent. The respective images are then selected and used for an enhanced presentation of the respective vessel segment to provide the clinician with targeted information about the vessel on both ends of the total occlusion. Due to experience, the clinician can then mentally interpolate and reconstruct the part of the vessel with the total occlusion.

The information about the vessel part with the total occlusion provided to the clinician can then be used to provide further analysis based on what is presented to the user. For example, a risk assessment or risk definition can be provided. The clinician can also decide on the further steps, e.g. regarding a possible treatment.

As an advantage, the user is provided with information about the vessel part with the total occlusion. As an effect, this facilitates, for example, planning of a treatment of the total occlusion. As another effect, for example, this also facilitates navigating through the total occlusion during the treatment, and also navigating towards the total occlusion. Thus, spatial guidance information is provided based on 2D images of the angiographic sequence. The user is supported, since the tedious observation of a loop-like presentation with faint contrast reappearance otherwise required is replaced by the more snap-shot like presentation of the processed image data focusing on the relevant image data.

In an example, it is provided to automatically display a static and more readable version of the information of interest, a so-called CTO snapshot. In one option, it is provided to automatically show a zoomed image of the region of the image.

Even though the (crucial) information of interest is local, faint, and moving dynamically with the cardiac motion in the sequence of images, the guidance image provides a more static snapshot-type image.

As an advantage, the clinician is provided with great help in performing one of the most difficult percutaneously coronary interventions. An example for the field of use is chronic total occlusion (OCT) treatments in percutaneously coronary interventions (PCI). This can be applied to X-ray imaging systems, such as C-arm based systems.

According to an aspect, a device for guidance for treatment of a chronic total occlusion is provided that comprises an image supply, a data processor and an output. The image supply provides a sequence of angiographic images comprising a vascular structure. The data processor detects at least one portion of the vascular structure indicating a total occlusion of a vessel based on the sequence of angiographic images; and determines an image of the sequence of images that shows at least one segment of the vessel next to the total occlusion; and generates guidance image data based on the determined image. The output provides the generated guidance image data. Thus, additional information relating to spatial aspects is provided to the user based on 2D image data.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
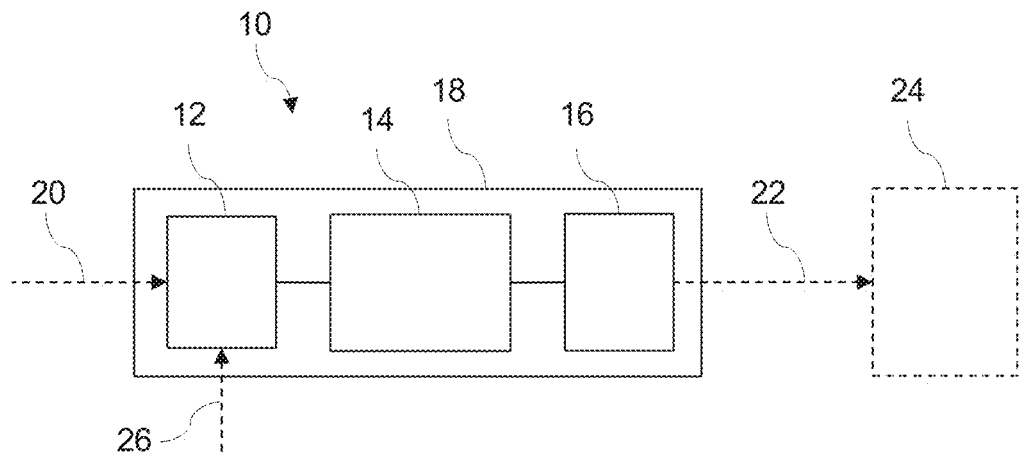
FIG. 1 schematically shows an example of a device for guidance for treatment of a chronic total occlusion.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 schematically shows an example of a device 10 for guidance for treatment of a chronic total occlusion. The device 10 comprises an image supply 12, a data processor 14 and an output 16. The image supply 12 is configured to provide a sequence of angiographic images comprising a vascular structure. The data processor 14 is configured to detect at least one portion of the vascular structure indicating a total occlusion of a vessel based on the sequence of angiographic images. The data processor 14 is also configured to determine an image of the sequence of images that shows at least one segment of the vessel next to the total occlusion. The data processor 14 is further configured to generate guidance image data based on the determined image. The output 16 is configured to provide the generated guidance image data.

In an example, the image supply 12, the data processor 14 and the output 16 are arranged in a common housing 18. In a further option, the image supply 12, the data processor 14 and the output 16 are arranged as separate components data-connected with each other.

An input arrow 20 indicates a supply of image data of the sequence of angiographic images. The supply can be provided from an imaging system or from a database which has stored image data provided by some imaging system.

An output arrow 22 indicates the provision (or output) of the generated guidance image data.

As an option, indicated with hashed lines, a display 24 is provided. The display 24 is configured to display the guidance image data as guidance information.

The term "guidance for treatment of a chronic total occlusion" relates to providing orientation and/or planning aid for treating a chronic total occlusion. The term may also relate to providing navigation during the treatment of a chronic total occlusion.

The image supply can also be referred to as image data supply, as image input, as input or as input unit. In an example, the image supply is data-connectable to an imaging source arrangement like an X-ray imaging apparatus. In an example, the image supply is data-connectable to a data storage having stored the sequence of angiographic images.

The data processor can also be referred to as data processing arrangement, as processor unit or as processor. In an example, the data processor is data-connected to the image supply and the output.

The output can also be referred to as output unit. In an example, the output is data-connectable to a display arrangement.

For example, the output is configured to provide the generated guidance image data to a clinician.

The term "angiographic images" relates to images in which the vascular structure is shown. In an example, the angiographic images are images of an at least partly contrast injected vasculature. The term "sequence of angiographic images" relates to a plurality of angiographic images, e.g. consecutively during the injection of contrast agent. The sequence of angiographic images is also referred to as angiographic sequence or angio sequence. The angiographic images are, for example, 2D X-ray images from the subject's anatomy of interest.

As a result, additional information is provided to the user based on the (2D) angiographic images. Thus, an alternative to X-ray computer tomography (CT-) based reconstructing imaging is provided. The way that the information is provided results in advantages for example in terms of required time and required resources, which contribute to economic benefits.

The presence of contrast agent downstream a total occlusion can be caused by alternative vascular connections forming a sort of by-passing flow. Further, the body may also adapt in reaction to a total occlusion and may provide additional vessels to provide sufficient blood flow also beyond, i.e. downstream (or distal), the total occlusion. In terms of cardiovascular structure, it is also possible that the body achieves a blood flow from one side (right or left) to the other side or vice versa. As a result, distal parts get blood flow and due to contrast agent, this may be faintly visible. As an example, for flow from one side to another, a so-called dual or bilateral injection may be provided. For example, if the left tree has a chronic total occlusion, the distal part of which is fed by the right coronary tree, the clinician can inject contrast agent in both trees in a timely manner, so that he/she can observe the proximal and the distal part of the chronic total occlusion in the same sequence (ideally, in the same image).

The term "downstream" refers to a location later in the direction of flow, e.g. distal to the occlusion. It can also be referred to as part of the vasculature that appears later in the sequence.

An example for detecting a portion of the vascular structure indicating a total occlusion of a vessel is that blood flow stops and then re-appears distal of the occlusion. By determining the end of the proximal part of the non-occluded portion of the vessel having the total occlusion and the beginning of the distal part, the chronic total occlusion can be determined.

The images of the angiographic sequence, also referred to as angios, can be taken prior to inserting or steering a guide wire inside the vasculature. The images of the angiographic sequence can also be any angio sequence taken during the intervention when the chronic total occlusion is visible.

In an example, the images of the angiographic sequence are acquired based on a viewing direction as selected or determined by the user in view of possible locations of total occlusions of the respective subject.

In an example, the data processor comprises a chronic total occlusion sequence detector configured to provide the detection of the at least one portion of the vascular structure indicating a total occlusion of a vessel based on the sequence of angiographic images. The chronic total occlusion sequence detector tells whether a given angiogram corresponds to a chronic total occlusion case and whether it shows the vessel segments downstream to the occlusion. This is needed to show the display when relevant only.

In an example, the data processor comprises a chronic total occlusion localization block configured to provide the determination of the region of the image to display. The chronic total occlusion localization block finds, e.g. automatically, the region of the images that comprises the vessel segments proximal and distal to the occlusion.

In an example, the data processor comprises a frame detector or frame aggregator. This block selects the most relevant frame or frames of the sequence to display, potentially filters them spatially and aggregates them temporally. In an example, the one frame is selected where the vessel segment distal to the occlusion is most visible. As an example, the final view is a cropped zoomed version of that frame.

In an example, the data processor comprises a sequence detector. The sequence detector provides the detection of at least one portion of the vascular structure indicating a total occlusion of a vessel.

The term "next to" refers to an image that is in close proximity to the total occlusion When the term "chronic total occlusion" is used, it is also referred to non-chronic total occlusions. It is referred in particular to long-term blocked and thus completely closed coronary vessels.

When the term "total occlusion" is used, it is referred to occlusions severe enough so that the guide wire cannot pass the stenosis. For example, the term refers to occlusions with a substantial closure, obstruction or blockage of the vessel. The term "substantial" is used in this context for an obstruction of at least 80% of the vessel's cross section still available for blood flow. In an example, the obstruction is of at least 90%, for example 95%. In an example, at least 99% are obstructed, such as 100%.

In an example, occlusions are targeted by the present invention. In an example, so-called 98%- or 99%-stenoses benefit in the sense that the proximal and distal portions appear with a delay in the angiographic images.

As an option, a zoomed aligned displaying is provided for further support. In an example, the complete obstruction relates to such an obstruction that a flow of blood injected with contrast agent is only hardly or not at all visible in the part of the obstruction on an X-ray image such as a fluorographic X-ray image.

In an example (not further shown in detail), the data processor is configured to determine a first image of the sequence of images that shows a segment of the vessel downstream to the total occlusion; and to generate guidance image data based on the determined first image.

As another example, the data processor is configured to detect an abnormally short branch. In an example, it is provided to use a model, as also explained for other examples below. In another example, this task is delegated to AI (artificial intelligence). The AI is trained by exemplary images sequences in which a clinician indicated where there is a CTO, and if so, localized it. Additionally, for training purposes, so-called negative examples are provided, i.e. non-CTO images, to learn how "normal" vessels look like. Accordingly, a trained AI algorithm may classify angiograms into CTO and non-CTO images.

In addition, optionally, the AI algorithm may provide localization of the CTO, that is, for a CTO image determine a location of the CTO, or a number of candidate locations if the CTO location cannot be established with a confidence level above a threshold.

In an additional or alternative option, the data processor is configured to determine an image of the sequence of images that shows a segment of the vessel upstream to the total occlusion; and to generate guidance image data based on the determined image.

In an example (not further shown in detail), for the detection of the at least one portion of the vascular structure indicating the total occlusion of a vessel, the data processor 14 is configured to compare the imaged vasculature with a projected model. Alternatively or in addition, the data processor 14 may be configured to identify determined vessel parts, measure a physical value and compare the measured value with a reference value. Alternatively or in addition, the data processor 14 may be configured to extrapolate branches and detect if extrapolated part matches contrast later in sequence. Alternatively or in addition, the data processor 14 may be configured to be trained with collection of chronic total occlusion angiograms and manually determined locations thereof and to apply this to new angiograms.

For example, the model projection refers to projecting and adapting a reference 3D model over the angiogram, and observing if the distal portion of a branch is missing.

For example, the (anatomical) branches from the vasculature displayed on the 2D image are identified, their length is measured, which is compared with reference physical values. The physical values may be normalized with the other branches length, for example, Further, it is decided whether they are too short.

For example, "interrupted" branches are identified. In an example, a given branch is extrapolated, e.g. without a model, but under the assumption that a branch is a continuous line. In case it can be observed that its "extrapolated part" meets contrast later in the sequence, this can be taken as an indication for a chronic total occlusion For example, the system is trained with a collection of chronic total occlusion angiograms, the localization of which has been manually determined. Artificial intelligence provides for the learning and application to new sequences.

As an example, the data processor 14 is configured to segment and label the branches in the angio and to identify branches that are abnormally short, based on the comparison with the model. In an alternative option, the data processor is configured to segment and label the branches in the angio and to identify branches that are abnormally short, based on threshold values derived from selected test data.

In an example, the data processor 14 is further configured to register the angiographic images to a model.

According to a first approach, a 3D geometrical model is projected onto the image, a branch by branch alignment is provided and occlusions are detected that way.

According to a second approach, the branches are segmented in the angiogram, the branches are labeled, for which a geometrical is not needed, and the length of each branch is established, which means still operating in 2D. In a final step, the measured length is compared with typical anatomical lengths. In an example, here it is decided that a branch may be abnormally short. As an advantage, it is not necessary to rely on a 3D coronary model for this approach.

However, in both approaches the image processing stays in the (2D) world of the sequence of angiographic images.

As an example, the angiographic images are used as taken and their perspective remains unchanged for being presented to the user. The image processing that is provided is based on at least one of the group of selecting images, zooming-in on selected images, cropping of images, toggling between images, blending in and out of images, enhancing images, e.g. regarding their contrast, intensity or brightness, and combining selected images.

In an example, instead of a smooth blending, a more static switching is provided.

In an example (not further shown in detail), the data processor 14 is further configured to determine a region of the image to be displayed based on the at least one portion of the vascular structure indicating the total occlusion. As an option, in addition or alternatively, the generating comprises a zooming-in of the determined first image.

The region of the image can also be referred to as the region of interest regarding the presentation of the guidance image data relating to the total occlusion.

In an example (not further shown in detail), the data processor 14 is further configured to determine a second image of the sequence of images that shows a segment of the vessel upstream to the total occlusion. The data processor 14 is further configured to use the first image and the second image for the generation of the guidance image data. Further, the generating comprises showing the first image and the second image, e.g. at the same time, overlaid, subsequently switching or subsequently fading in an out.

By showing the content of the first image and the second image, the user is provided with a visualization of only relevant images.

As an example, the first and the second image are combined. For example, the first and the second image are each cropped to show the respective vessel part and a part of the total occlusion. Stitched together, or otherwise combined, the complete vessel segment including the total occlusion becomes visible. As an example, fine image processing is provided. In an example, motion has been going on between both image acquisitions, e.g. due to cardiac, breathing etc., and it is provided to compensate for it to show a fair representation of the combined proximal and distal vessel segments.

In another example, the first image and the second image are provided in an overlaid manner as a blending in and out loop showing the first image, then continuously overlaying the second image, then continuously blending out the first image, then showing the second image, then then continuously overlaying the first image, then continuously blending out the second image, and back to showing the first image.

In an example, the generating comprises a zooming-in of the determined second image.

In an option, the zooming-in is combined with the presentation of the first image and the second image.

In an example, a zoomed switching is provided replacing a manual looping of a sequence.

In an example (not further shown in detail), to determine the first image, the data processor 14 is further configured to determine a plurality of first images showing the segment of the vessel downstream to the total occlusion; and to select at least one of the images as most relevant according to predetermined criteria comprising at least one parameter of the group of: visibility of the vessel segment, contrast, brightness, sharpness and resolution; and to use the selected at least one most relevant image for the generation of the guidance image data.

In an example, provided in addition or alternatively, to determine the second image, the data processor 14 is further configured to determine a plurality of second images showing the segment of the vessel upstream to the total occlusion; and to select at least one of the images as most relevant according to predetermined criteria comprising at least one parameter of the group of: visibility of the vessel segment, contrast, brightness, sharpness and resolution; and to use the selected at least one most relevant image for the generation of the guidance image data.

In an example (not further shown in detail), the data processor 14 is configured to determine an image of the sequence of images that shows both a segment of the vessel downstream to the total occlusion and a segment of the vessel upstream to the total occlusion. The data processor 14 is also configured to generate guidance image data based on the determined image. Both vessel parts are visible in the one image, i.e. proximal and distal end are visible on one unique image. The determined one image is also referred to as unique image or dual use image. In an example, algorithmic work is provided to detect the appropriate region, zoom on it, and optionally perform some denoising/boosting. In an example (not further shown in detail), the data processor 14 is further configured to spatially filter the selected images; and to use the spatially filtered images for the generation of the guidance image data.

As an example, it is provided to rely on identifying one image for providing help for guidance.

In an example, one image with both ends of the occlusion is identified, when such an image exists, i.e. when possible.

In a further example, if an image with both occlusion ends visible cannot be found, it is provided to try to identify two images having one segment each.

In a still further example, if an image with both occlusion ends visible cannot be found, it is provided to try to identify one image with one segment only.

In addition or alternatively, the data processor 14 is further configured to temporarily align the spatially filtered images and to combine the temporarily aligned images; and use them for the generation of the guidance image data.

In an example (not shown), the data processor 14 comprises a region-of-an image detector. The region of the image detector provides the determination of the region of the image to be displayed based on the at least one portion of the vascular structure indicating the total occlusion. In an example, the data processor 14 comprises an image aggregator. The image aggregator provides the temporal alignment of the spatially filtered images and the combination of the temporally aligned images. The image aggregator can also be referred to as frame aggregator. In an example, motion compensation is provided for the aggregation.

The spatial filtering results in cleaner and more contrasted images to be displayed. For a clean image, pixel values can be averaged. Noise filtering can be provided to find only pixels inside the vessel and to filter these. Segmentation can be provided to take only those pixels for averaging. The aggregation can be provided with zooming-in for localization purposes.

In an example, contrast of two images is combined to form one static image.

In an example (indicated in FIG. 1 as an option), examination context data 26 is provided. The data processor 14 is configured to take the examination context data into account for the detection of the at least one portion of the vascular structure indicating a total occlusion.

The examination context data comprises at least one of the group of previous image data, outcome of previous examination or intervention and indicators for possible locations of the total occlusion within the vascular structure. Another input that also provides some indications is a rather long acquisition duration and thus a large number of images of the sequence of angiographic images.

In an example (not further shown in detail), the data processor 14 is further configured to initially determine if a total occlusion is shown in the vascular structure presented by the sequence of angiographic images.

If a total occlusion is present, the location detection is provided. For example, if a distal segment of a vessel, i.e. distal of the occlusion, is not visible, the clinician would also not have enough information for further guidance. Then, a guidance of a guidewire or a catheter through the total occlusion cannot be performed.

In an example, the classification of a sequence as being class A or B, i.e. whether a total occlusion like a chronic total occlusion is present or not, is provided by an artificial intelligence module. The two types of classes can also be referred to as CTO images or non-CTO images.

Figure 2:
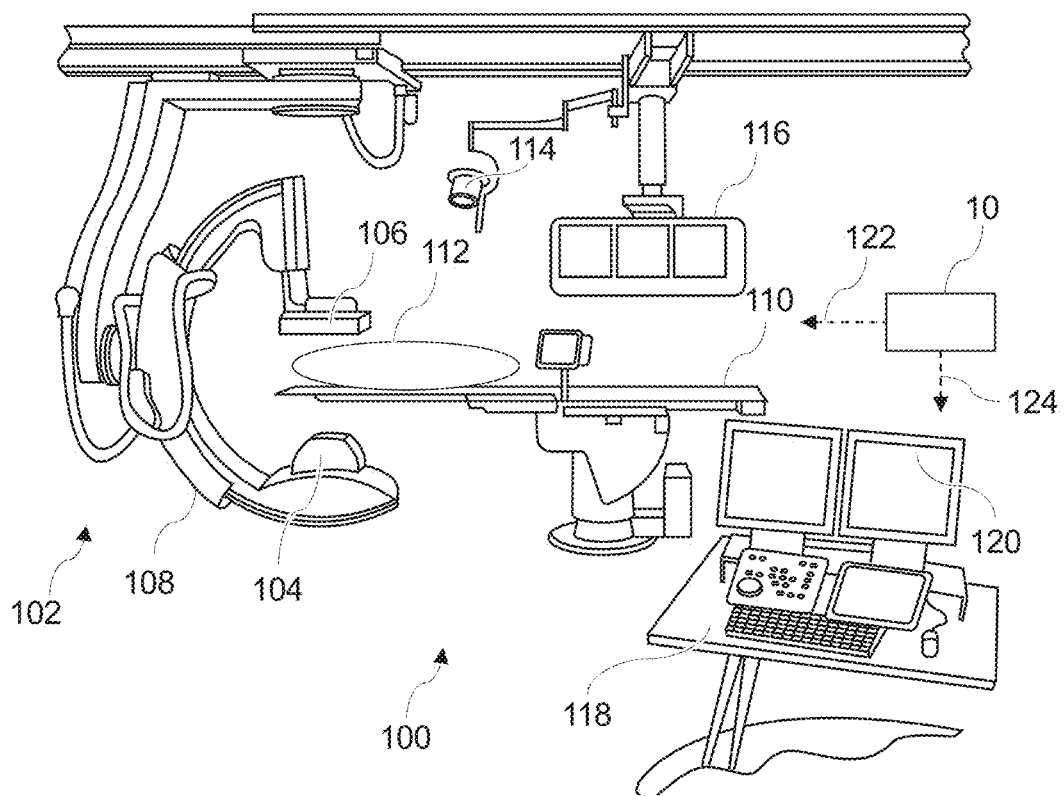
FIG. 2 shows an example of a system for guidance for treatment of a chronic total occlusion with an X-ray imaging arrangement.

FIG. 2 shows an example of a system 100 for guidance for treatment of a chronic total occlusion with an X-ray imaging arrangement 102. The system 100 also comprises an example of the device 10 for guidance for treatment of a chronic total occlusion according to one of the examples described above and below. The X-ray imaging arrangement 102 is configured to provide the sequence of angiographic images.

As an example, the X-ray imaging arrangement 102 is provided as a stationary movable X-ray system comprising an X-ray source 104 and a detector 106 arranged on two opposing ends of a C-arm 108 movably supported from a ceiling support. In further examples, different types of X-ray imaging system are used, such as mobile X-ray systems or non-C-arm system. A support 110 is provided such that a subject 112 can be arranged thereon for imaging and other purposes. Further, lighting equipment 114 is shown and also a display arrangement 116. A console arrangement 118 is shown in the foreground which comprises displays 120 and other user interface devices such as keyboard, control panel, tablet and mouse. The device 10 for guidance for treatment of a chronic total occlusion is data connected to the X-ray imaging arrangement 102, as indicated with first hashed arrow 122. The device 10 for guidance for treatment of a chronic total occlusion is also data connected to the console arrangement 118, as indicated with second hashed arrow 124.

Figure 3:
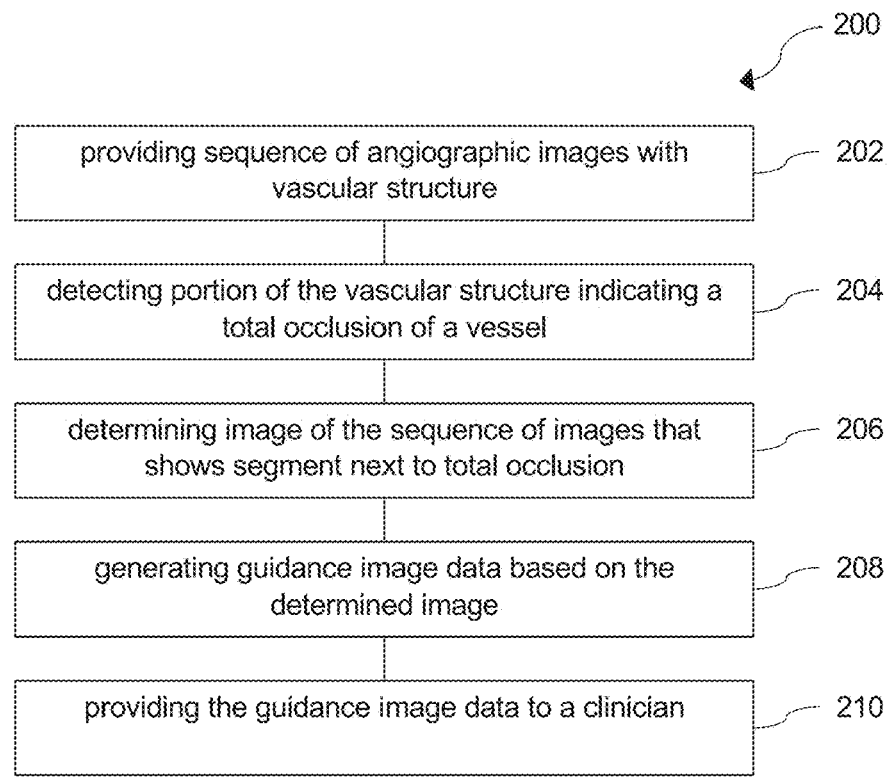
FIG. 3 shows basic steps of an example of a method for guidance for treatment of a chronic total occlusion.

FIG. 3 shows basic steps of an example of a method 200 for guidance for treatment of a chronic total occlusion. The method 200 comprises the following steps:

In a first step 202, a sequence of angiographic images comprising a vascular structure is provided. In a second step 204, at least one portion of the vascular structure indicating a total occlusion of a vessel based on the sequence of angiographic images is detected. In a third step 206, an image of the sequence of images that shows at least one segment of the vessel next to the total occlusion is determined. In a fourth step 208, guidance image data is generated based on the determined image. In a fifth step 210, the guidance image data is provided to a clinician.

In an example, the determining comprises determining a first image of the sequence of images that shows a segment of the vessel downstream to the total occlusion. The first image is thus an image that is relating to the downstream side of the occlusion and that is approximate or close to the total occlusion, where the vessel is (still) visible in the angiographic image. For example, the first image is the downstream image closest to the total occlusion. The first image is thus a downstream image.

In an example, the generating comprises a zooming-in of the determined first image.

In an example, the method 200 further comprises the step of displaying the guidance image data as guidance information.

According to an example not further shown in detail, the method 200 further comprises the step of spatially filtering the selected images. The spatially filtered images are used for the generating of the guidance image data.

As an option, the method 200 further comprises the step of temporarily aligning the spatially filtered images. The temporarily aligned images are combined and used for the generating of the guidance image data.

The temporal alignment and the combination can also be referred to as image aggregation.

As a further option, the method 200 further comprises the step of determining a second image of the sequence of images that shows a segment of the vessel upstream to the total occlusion. As a further option, the first and the second image are used for generating the guidance image data.

In an option, the two steps of region of the image detection and alignment are combined. The region of the image is meaningless on some images, for instance, the non-injected ones, and, in an example, those images are ignored by the selection process, anyway. In an example, a learning algorithm proposes regions of image on each image and generates an associated quality score, which can then be exploited in the image selection process.

In an example, the sequence is temporally filtered around the selected frame $f_{dist}$ in order to further improve the contrast of the vessel portion of interest. This provides a sort of vessel boost.

In another example, a second frame $f_{prox}$ is selected where the vessel segment proximal to the occlusion is most visible. The corresponding zoomed region is filtered spatially and/or temporally. Then, both zoomed regions (corresponding to $f_{dist}$ and $f_{prox}$ are shown on separate displays. Or they are aligned and combined, so as to show on the same view both occlusion extremities.

The second image is an image that is relating to the upstream side of the occlusion and that is approximate or close to the total occlusion, where the vessel is (still) visible in the angiographic image. For example, the second image is the upstream image closest to the total occlusion. The second image is thus an upstream image.

Figure 4:
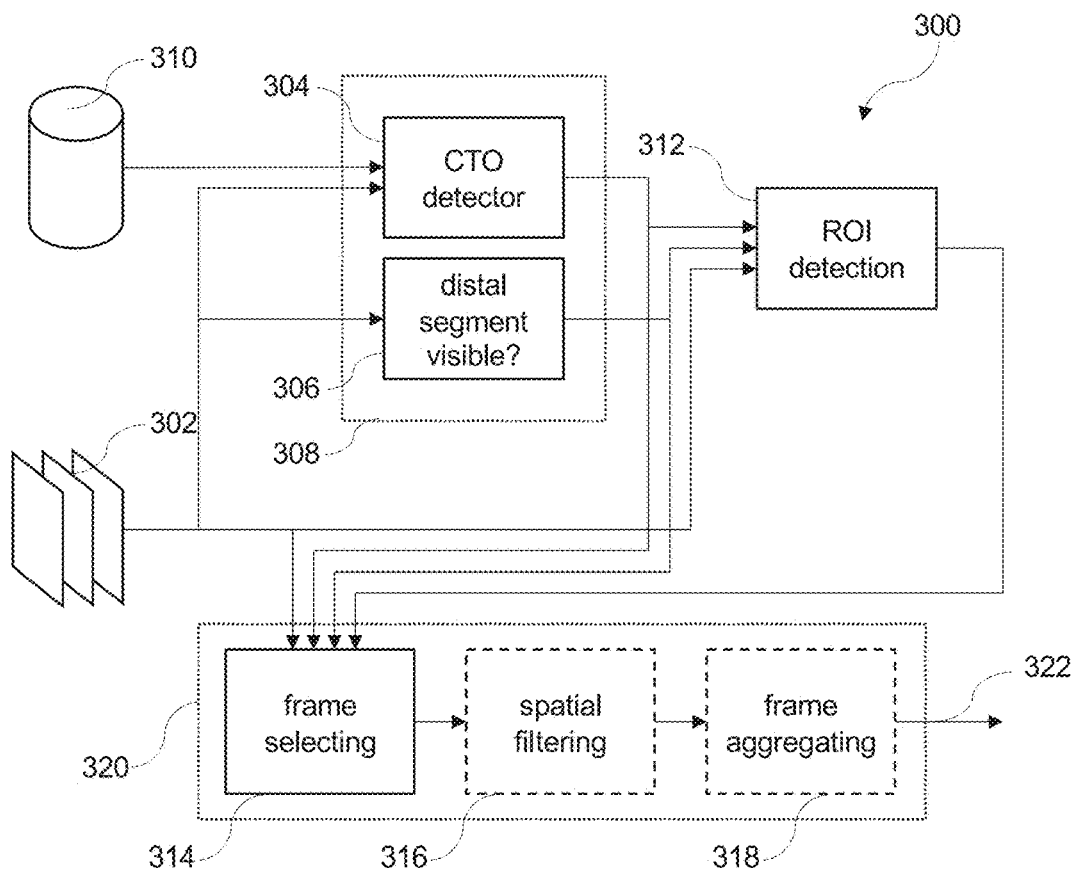
FIG. 4 schematically shows a further example of a concept for guidance for treatment of a chronic total occlusion.

FIG. 4 schematically shows a further example of a concept 300 for guidance for treatment of a chronic total occlusion. Image data of an angiographic sequence 302 is provided to a CTO detector 304, indicated as first frame, which detects if a total occlusion is present in the images. In an example, all images of the sequence are subject to the analyses 302 and 304. Further, a second frame 306 is provided to determine if a distal segment is visible. A dotted frame 308 indicates that the first and the second frame can be provided in an integrated manner. As an option, exam content 310 is provided to the CTO detector 304. The data is provided to a third frame 312 for detection of the region of the image. As next image processing step, a frame selection 314 is provided, and optional spatial filtering 316 and frame aggregating 318. The frame selection 314, the spatial filtering 316 and the frame aggregating 318 can be provided in an integrated manner, as indicated by dotted frame 320. An arrow 322 indicates the output.

It is noted that the connecting lines between the frames indicate a supply of the respective data.

Figure 5:
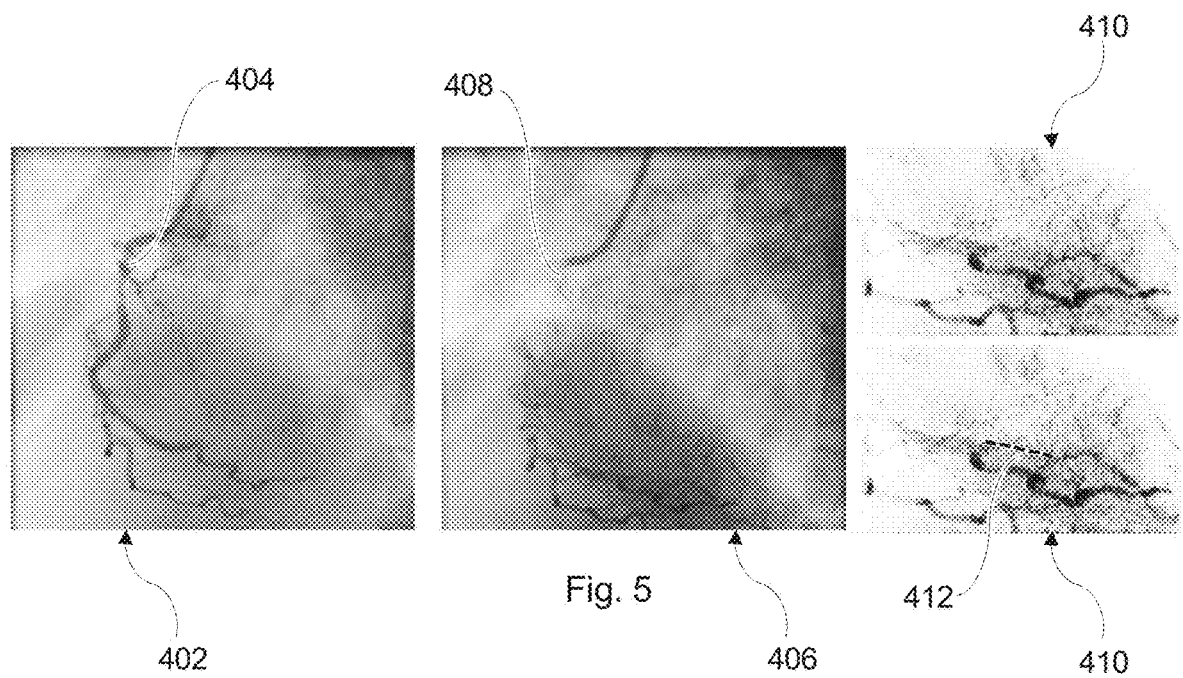
FIG. 5 illustrates an example of an angiogram showing occlusions in the left part, an angiogram where the vessel part distal to the lesion is faintly visible in the middle part and two zoomed-in images of the considered region in the right part, with an interpolated occluded vessel course in the bottom image on the right.

FIG. 5 illustrates an example of a first angiogram 402 in the left part of FIG. 5. The angiogram 402 shows occlusions 404. In the middle part of FIG. 5, a second angiogram 406 is shown, where a vessel part 408 distal to the lesion is faintly visible. In the upper right part of FIG. 5, a first zoomed-in image 410 of the considered region is shown. In the lower right part of FIG. 5, the zoomed-in image 410 is provided with an interpolated occluded vessel course 412.

Figure 6:
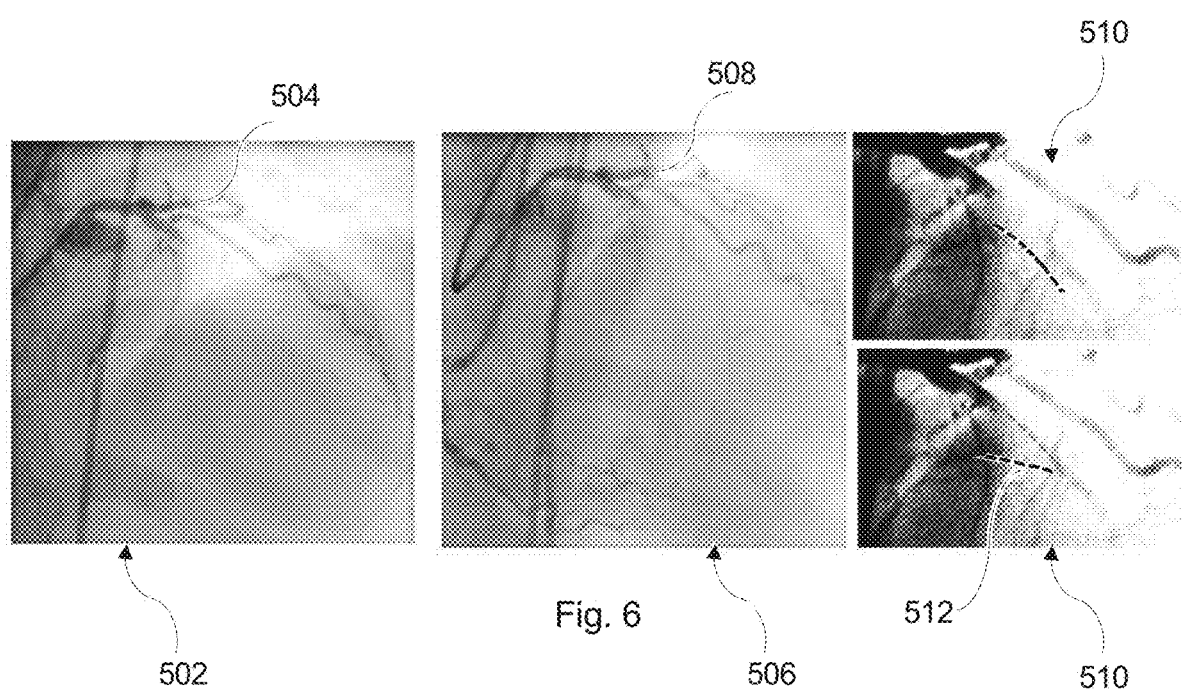
FIG. 6 illustrates another example of an angiogram showing occlusions in the left part, an angiogram where the vessel part distal to the lesion is faintly visible in the middle part and two zoomed-in images of the considered region in the right part, with an interpolated occluded vessel course in the bottom image on the right.

FIG. 6 illustrates another example of a first angiogram 502 in the left part of FIG. 6. The angiogram 502 shows occlusions 504. In the middle part of FIG. 6, a second angiogram 506 is shown, where the vessel part distal to the lesion is faintly visible. In the upper right part of FIG. 6, a first zoomed-in image 508 of the considered region is shown. In the lower right part of FIG. 6, the zoomed-in image 508 is provided with an interpolated occluded vessel course 510.

In an example, the first image, i.e. the downstream image, is a distal image. The term distal is used in relation to the subject's anatomy, wherein distal relates to a location further away from the center of the body, e.g. further away from the heart in terms of the blood flow passage.

In an example, the second image, i.e. the upstream image, is a proximal image. The term proximal is used in relation to the subject's anatomy, wherein proximal relates to a location closer to the center of the body, e.g. closer to the heart in terms of the blood flow passage.

In an example, the method is further comprising the step of determining a region of the image to be displayed based on the at least one portion of the vascular structure indicating the total occlusion.

In an example, determining the first image comprises determining a plurality of first images showing the segment of the vessel downstream to the total occlusion. The method is comprising the step of selecting at least one of the images as most relevant according to predetermined criteria comprising at least one parameter of the group of: visibility of the vessel segment, contrast, brightness, sharpness and resolution. The selected at least one most relevant image is used for the generating of the guidance image data.

The plurality of images is also referred to as a plurality of frames.

In an example, the following steps are provided: a sequence detector step, a region of the image detector step and a frame aggregator step. The sequence detector step decides whether the considered sequence is relevant to produce a chronic total occlusion snapshot. As an example, it is assessed and verified i) that the angiogram refers to a chronic total occlusion, and ii) that the vessel segment distal to the occlusion is visible on the angiogram. In an example, the first aspect is decided by image processing techniques, by comparing the imaged vasculature with a projected healthy heart model. For example, the branches in the angiographic sequence are segmented and labelled, and branches are identified that are abnormally short. As another example, an artificial intelligence (AI) method is provided and the aspects are assessed and verified by training a network that classifies angiograms into CTO images and non-CTO images. In an example, the second aspect is also solved by image processing techniques. Once branches have been segmented and labelled, and an abnormally short one has been selected, the proximal part of the occlusion is known. It is then looked further in the branch direction to see whether faint contrast appears later in the angiogram sequence. In AI terms, the angiograms can be labelled accordingly. In particular, particularly long angiograms can provide good hints that the clinician is expecting that contrast will reappear further in the vasculature.

The region of the image detector step has the goal to define which spatial region of each image is displaying the relevant information, i.e. the beginning and the end of the occlusion. In other words, a region is determined around the location of the CTO, comprising both the proximal and the distal part of the vessel of interest around the occlusion. In an example, this could be based on the previously described image processing. If the previous steps have been performed by the proposed approach, the proximal part of the occlusion would be identified on one image (tip of the abnormally short branch), and the distal part would have been identified on a later image (work already done in the sequence detector step). Both these aspects could serve as an initialization of a region of the image, identical all over the sequence. In an example, this is refined by tracking methods all over the sequence. Alternatively, it is also provided to train an AI algorithm to determine this region of the image based on examples on many angiograms.

The frame aggregator step determines which image, also referred to as frame, or group of frames will be cropped on the detected region, how it will be enhanced (or left untouched), and how the different selected and enhanced regions will be combined. Different embodiments are possible. In an example, this step selects one frame $f_{dist}$ where the vessel segment distal to the occlusion is most visible. It could optionally be spatially filtered in order to improve the segment visibility.

In an example, a computer program or program element for controlling an apparatus according to one of the examples above is provided, which program or program element, when being executed by a processing unit, is adapted to perform the method steps of one of the method examples above.

The term "subject" may also be referred to as individual. The "subject" may further also be referred to as patient, although it is noted that this term does not indicate whether any illness or disease is actually present with the subject.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for guidance for treatment of a chronic total occlusion, the device comprising:
   a processor configured to:
      obtain a sequence of angiographic images comprising a vascular structure with a total occlusion of a vessel, wherein a course of the vascular structure at the total occlusion is not visible in the sequence of angiographic images;
      detect that the total occlusion of the vessel is present in a first image of the sequence of angiographic images, the first image including a first segment of the vessel indicating a start of the course;
      determine a second image that shows a second segment of the vessel next to the total occlusion, the second segment indicating an end of the course; and
      generate guidance image data, based on the first image and the second image, that indicates the course of the vascular structure that is not visible in the sequence of angiographic images.

2. The device according to claim 1, wherein the processor is further configured to:
   determine the second image of the sequence of images shows a segment of the vessel downstream to the total occlusion; and
   generate guidance image data based on the segment of the vessel downstream to the total occlusion.

3. The device according to claim 1, wherein, to determine that the portion of the vascular structure includes the total occlusion of the vessel, the processor is further configured to at least one of:
   compare the vascular structure with a projected model;
   identify vessel parts of the vessel, measure a physical value, and compare the measured physical value with a reference value;
   extrapolate branches and detect if the extrapolated branches match contrast later in the sequence of angiographic images;
   obtain a collection of angiograms with chronic total occlusions and manually determined locations of the chronic total occlusions in the collection of angiograms; and
   apply the determined locations to detect chronic total occlusions in new angiograms.

4. The device according to claim 1, wherein the processor is further configured to determine a region of the second image to be displayed based on the portion of the vascular structure that includes the total occlusion,
   wherein the generation of the guidance image data comprises a zooming-in of the second image.

5. The device according to claim 2, wherein the processor is further configured to:
   determine a third image of the sequence of images that shows a segment of the vessel upstream to the total occlusion; and
   generate the guidance image data based on the first image, the second image, and the third image and the generated image data comprises showing the second image and the third image.

6. The device according to claim 1, wherein, to determine the second image, the processor is further configured to:
   determine a plurality of second images showing the segment of the vessel downstream to the total occlusion;
   select at least one of the second images as most relevant according to predetermined criteria comprising at least one of: visibility of the segment of the vessel downstream to the total occlusion, contrast, brightness, sharpness, and resolution; and
   use the selected at least one most relevant image for the generation of the guidance image data.

7. The device according to claim 1, wherein the processor is further configured to:
   determine a fourth image of the sequence of images that shows both a segment of the vessel downstream to the total occlusion and a segment of the vessel upstream to the total occlusion; and
   use the fourth image for the generation of the guidance image data.

8. The device according to claim 6, wherein the processor is further configured to spatially filter the selected at least one of the second images and use the spatially filtered at least one of the second images for the generation of the guidance image data.

9. The device according to claim 6, wherein the processor is further configured to:
   temporally align the selected at least one of the second images;
   combine the temporally aligned at least one of the second images; and
   use the combined temporally aligned at least one of the second images for the generation of the guidance image data.

10. The device according to claim 1, wherein the processor is further configured to determine that the portion of the vascular structure includes the total occlusion based on examination context data.

11. The device according to claim 1, wherein the processor is further configured to initially determine if the total occlusion is shown in the vascular structure presented by the sequence of angiographic images.

12. The device according to claim 1, further comprising a display configured to display the guidance image data as guidance information.

13. A system for guidance for treatment of a chronic total occlusion, the system comprising:
the device of claim 1; and
an X-ray imaging arrangement configured to provide the sequence of angiographic images.

14. A method for guidance for treatment of a chronic total occlusion, the method comprising:
providing a sequence of angiographic images comprising a vascular structure with a total occlusion of a vessel, wherein a course of the vascular structure at the total occlusion is not visible in the sequence of angiographic images;
detecting that a total occlusion of the vessel is present in a first image of the sequence of angiographic images, the first image including a first segment of the vessel indicating a start of the course;
determining a second image that shows a second segment of the vessel next to the total occlusion, the second segment indicating an end of the course; and
generating guidance image data, based on the first image and the second image, that indicates the course of the vascular structure that is not visible in the sequence of angiographic images.

15. A non-transitory computer-readable storage medium having stored a computer program comprising instructions, which, when executed by a processor, cause the processor to:
provide a sequence of angiographic images comprising a vascular structure with a total occlusion of a vessel, wherein a course of the vascular structure at the total occlusion is not visible in the sequence of angiographic images;
detect that a total occlusion of a vessel is present in a first image of the sequence of angiographic images, the first image including a first segment of the vessel indicating a start of the course;
determine a second image that shows a second segment of the vessel next to the total occlusion, the second segment indicating an end of the course; and
generate guidance image data, based on the first image and the second image, that indicates the course of the vascular structure that is not visible in the sequence of angiographic images.

16. The method according to claim 14, further comprising:
determining at least one of:
a third image of the sequence of images that shows a segment of the vessel downstream to the total occlusion, or
a fourth image of the sequence of images that shows a segment of the vessel upstream to the total occlusion; and
generating the guidance image data based on at least one of the third image or the fourth image.

17. The method according to claim 14, further comprising:
comparing the vascular structure with a projected model;
identifying vessel parts of the vessel, measuring a physical value, and comparing the measured physical value with a reference value;
extrapolating branches and detecting if the extrapolated branches match contrast later in the sequence of angiographic images;
obtaining a collection of angiograms with chronic total occlusions and manually determining locations of the chronic total occlusions in the collection of angiograms; and
applying the determined locations to detect chronic total occlusions in new angiograms.

18. The non-transitory computer-readable storage medium according to claim 15, wherein the instructions, when executed by the processor, further cause the processor to:
determine at least one of:
a third image of the sequence of images that shows a segment of the vessel downstream to the total occlusion, or
a fourth image of the sequence of images that shows a segment of the vessel upstream to the total occlusion; and
generate the guidance image data based on at least one of the third image or the fourth image.

19. The non-transitory computer-readable storage medium according to claim 15, wherein the instructions, when executed by the processor, further cause the processor to:
compare the vascular structure with a projected model;
identify vessel parts of the vessel, measure a physical value, and compare the measured physical value with a reference value;
extrapolate branches and detect if the extrapolated branches match contrast later in the sequence of angiographic images;
obtain a collection of angiograms with chronic total occlusions and manually determine locations of the chronic total occlusions in the collection of angiograms; and
apply the determined locations to detect chronic total occlusions in new angiograms.

20. The non-transitory computer-readable storage medium according to claim 15, wherein the instructions, when executed by the processor, further cause the processor to:
determine a plurality of third images showing the segment of the vessel downstream to the total occlusion;
select at least one image of the plurality of third images as most relevant according to predetermined criteria comprising at least one of: visibility of the segment of the vessel downstream to the total occlusion, contrast, brightness, sharpness, and resolution; and
use the selected at least one most relevant image for the generation of the guidance image data.

* * * * *